US009334174B2

(12) United States Patent
Kobiro et al.

(10) Patent No.: US 9,334,174 B2
(45) Date of Patent: May 10, 2016

(54) METHOD FOR SYNTHESIZING SPHERICAL POROUS TITANIUM OXIDE NANOPARTICLES, SPHERICAL POROUS TITANIUM OXIDE NANOPARTICLES PRODUCED BY SAID SYNTHESIS METHOD, AND CARRIER FOR GENE GUN WHICH COMPRISES SAID SPHERICAL POROUS TITANIUM OXIDE NANOPARTICLES

(75) Inventors: Kazuya Kobiro, Kochi (JP); Pengyu Wang, Kochi (JP); Takeshi Ohama, Kochi (JP)

(73) Assignee: KOCHI UNIVERSITY OF TECHNOLOGY, Kochi (JP)

(*) Notice: Subject to any disclaimer, the term of this patent is extended or adjusted under 35 U.S.C. 154(b) by 85 days.

(21) Appl. No.: 14/353,132

(22) PCT Filed: Jan. 27, 2012

(86) PCT No.: PCT/JP2012/051884
§ 371 (c)(1),
(2), (4) Date: Jun. 13, 2014

(87) PCT Pub. No.: WO2013/061621
PCT Pub. Date: May 2, 2013

(65) Prior Publication Data
US 2014/0335356 A1    Nov. 13, 2014

(30) Foreign Application Priority Data

Oct. 26, 2011   (JP) .................. 2011-235367

(51) Int. Cl.
*C01G 23/053*    (2006.01)
*C12N 15/89*    (2006.01)
*B82Y 5/00*    (2011.01)
*B82Y 40/00*    (2011.01)

(52) U.S. Cl.
CPC ............ *C01G 23/053* (2013.01); *C12N 15/895* (2013.01); *B82Y 5/00* (2013.01); *B82Y 40/00* (2013.01); *C01P 2002/72* (2013.01); *C01P 2004/04* (2013.01); *C01P 2004/32* (2013.01); *Y02P 20/544* (2015.11); *Y10S 977/773* (2013.01); *Y10S 977/896* (2013.01); *Y10S 977/916* (2013.01); *Y10T 428/2982* (2015.01)

(58) Field of Classification Search
CPC ................ C01G 23/047–23/08; C12N 15/895; Y02P 20/544; Y10T 428/2982; B82Y 5/00; B82Y 40/00; Y10S 977/773; Y10S 977/916; Y10S 977/896; C01P 2004/04; C01P 2004/32; C01P 2002/72
USPC ....................................................... 423/610
See application file for complete search history.

(56) References Cited

U.S. PATENT DOCUMENTS

| 2006/0115411 A1* | 6/2006 | Jensen | ...................... B01J 3/008 423/611 |
| 2012/0202120 A1* | 8/2012 | Kim | ........................ B82Y 30/00 429/231.1 |

FOREIGN PATENT DOCUMENTS

| JP | 10130003 A | 5/1998 |
| JP | 2003164289 A | 6/2003 |
| JP | 2006512264 A | 4/2006 |
| JP | 2009518167 A | 5/2009 |

OTHER PUBLICATIONS

Kim et al., "Continuous Synthesis of Surface-Modified Metal Oxide Nanoparticles Using Supercritical Methanol for Highly Stabilized Nanofluids," Chem. Mater. 2008, 20, 6301-6303.*
Veriansyah et al., "Continuous synthesis of surface-modified zinc oxide nanoparticles in supercritical methanol," J. of Supercritical Fluids 52 (2010) 76-83.*
Z. Liu et al. *One-Steo Fabrication and High Photocatalytic Activities of $TiO_2$ Hollow Aggregates by Using a Low-Temperature Hydrothermal Method Without Templates* Chem. Eur. J. 2007, 13, pp. 1851-1855.
Z. Lu et al. *Mesoporous $TiO_2$ Nanocrystal Cluster for Selective Enrichment of Phosphopeptides* Anal. Chem., 2010, 82, pp. 7249-7257; Angew. Chem. Int. Ed. 2010, 49, 1862.
Z. Lu et al. *Self-Assembled $TiO_2$ Nanocrystal Cluster for Selective Enrichment of Phosphopeptides Proteins* Communications, 2009, pp. 1862-1866.
W.G. Yang et al. *Contolling Synthesis of Well-Crystallized Mesoporous Microspheres $Tio_2$ Microspheres with Ultrahigh Surface Area for High-Performance Dye-Sensitized Solar Cells* J.Mater. Chem. 2010, 20, pp. 2870-2876.
T. Togashi et al. *Surfactant-Assisted One-Pot Synthesis of Superparamagnetic Magnetite Nanoparticle Cluster with Tunable Cluster Size and Magnetic Field Sensitivy* J. Am. Chem. Soc. 2007, 129, 11061, Dalton Trans., 2011, 40, pp. 1073-1078.
T. Arita et al. *Super Hydrothermal Synthesis of Carboxylic Acid—Surface-Functionalized $TiO_2$ Nanocrystals: pH Sensitive Dispersion and Hybridization with Organic Compounds* J. Nanoparticle Res 2007, 9, 1067; Chem Lett. 2010, 39, pp. 961-963.

(Continued)

*Primary Examiner* — Anthony J Zimmer
(74) *Attorney, Agent, or Firm* — The Dobrusin Law Firm, P.C.

(57) ABSTRACT

Problem. Provided are a method for synthesizing spherical porous titanium oxide nanoparticles, which is easy to operate, does not take a long time for synthesis, and can easily adjust the particle diameter and the pore diameter of the spherical porous titanium oxide nanoparticles in accordance with the application thereof; spherical porous titanium oxide nanoparticles produced by the synthesizing method; and a gene gun carrier consisting of the spherical porous titanium oxide nanoparticles. Solution. A method for synthesizing spherical porous titanium oxide nanoparticles, includes: a step of reacting titanium isopropoxide and carboxylic acid in supercritical fluid, wherein the supercritical fluid is supercritical methanol, and the carboxylic acid is formic acid, acetic acid, benzoic acid, o-phthalic acid, fumaric acid, or maleic acid.

15 Claims, 15 Drawing Sheets

(56) References Cited

OTHER PUBLICATIONS

D. Rangappa et al., *Transparent $CoAl_2O_4$ Hybrid Nano Pigment by Organic Ligand-Assisted Supercritical Water* Articles 2007, vol. 127, No. 36, pp. 11061-11066.

T. Mousavand et al., *Organic-Ligand-Assisted Supereritical Hydrothermal Synthesis of Titanium Oxide Nanocrystals Leading to Perfectly Dispersed Titanium Oxide Nanoparticle in Organic Phase* Research Paper 2007, pp. 1067-1071.

International Search Report dated Apr. 24, 2012; Application No. PCT/JP2012/051884.

International Preliminary Report, Application No. PCT/JP2012/051887 dated Apr. 29, 2014.

* cited by examiner

TEM (Transmission Electron Microscope) pictures

TEM (Transmission Electron Microscope) pictures

EDX mapping

METHOD FOR SYNTHESIZING SPHERICAL POROUS TITANIUM OXIDE NANOPARTICLES, SPHERICAL POROUS TITANIUM OXIDE NANOPARTICLES PRODUCED BY SAID SYNTHESIS METHOD, AND CARRIER FOR GENE GUN WHICH COMPRISES SAID SPHERICAL POROUS TITANIUM OXIDE NANOPARTICLES

CLAIM OF PRIORITY

This application is a 371 of international PCT/JP2012/051884, filed on Jan. 27, 2012, which claims benefit to Japanese serial number 2011-235367 filed on Oct. 26, 2011, which are both hereby entirely incorporated by reference for all purposes.

TECHNICAL FIELD

The present invention relates to a method for synthesizing spherical porous titanium oxide nanoparticles, spherical porous titanium oxide nanoparticles produced by the synthesizing method, and a gene gun carrier consisting of the spherical porous titanium oxide nanoparticles.

BACKGROUND OF THE INVENTION

In recent years, porous nanoparticles are used in various applications such as adsorption, separation, and catalyst. Porous nanoparticles refers to nanoparticles having a pore of 2-50 nm diameter (mesopore). In particular, porous nanoparticles of titanium oxide are mainly used for white pigment, catalyst support, optical catalyst, reaction catalyst, optical semiconductor, solar battery, etc. since they have unique optical properties, optoelectronic properties, biological properties, sustained releasability, electrical properties, and chemical properties.

Because of their spherical shape, it has become clear that the porous titanium oxide nanoparticles exhibit excellent properties such as excellent stability, excellent dispersibility, high light harvesting characteristics, and easy reuse. Hydrothermal method, sol-gel method, self-aggregation (self-organization) method, and the like are conventionally used as a method for synthesizing spherical porous titanium oxide nanoparticles.

Non-Patent Document 1 describes a method for synthesizing spherical porous titanium oxide nanoparticles used for optical catalyst using the hydrothermal method. Specifically, Non-Patent Document 1 describes a method that $Ti(SO_4)_2$, $NH_4F$, and $H_2O$ are reacted for six hours at the temperature of 160° C. so as to synthesize spherical porous titanium oxide nanoparticles.

Non-Patent Document 2 describes a method for synthesizing spherical porous titanium oxide nanoparticles used for solar battery using the sol-gel method. Specifically, Non-Patent Document 2 describes a method that $Ti(OC_4H_9)_4$ and diethylene glycol are stirred in acetone for eight hours, and then centrifuged for 1 hour so as to synthesize spherical porous titanium oxide nanoparticles. Non-Patent Document 3 describes a method for synthesizing spherical porous titanium oxide nanoparticles used in biochemistry (drug delivery) using the self-aggregation (self-organization) method. Specifically, Non-Patent Document 3 describes a method that titanium oxide particles are aggregated, coated with $SO_2$ to form a cluster, and then calcinated and silica-etched so as to synthesize spherical porous titanium oxide nanoparticles.

However, there is a problem that these conventional synthesizing methods are very complicated, and thus take a long time for synthesis.

A method for synthesizing spherical porous nanoparticles in supercritical fluid has also been known. Non-Patent Document 4 describes a method for synthesizing spherical porous $Fe_3O_4$ nanoparticles in supercritical fluid, and Non-Patent Document 5 describes a method for synthesizing spherical porous $TiO_2$ nanoparticles in supercritical fluid. A method for synthesizing spherical porous titanium oxide nanoparticles using titanium isopropoxide and an organic modifying agent in supercritical fluid is also known. Hexanoic add, hexanal, decylphosphonic add, and the like are known as the organic modifying agent. These methods for synthesizing spherical porous nanoparticles in supercritical fluid use one-pot synthesis and thus have advantages of short reaction time and easy operation. However, in these synthesizing methods, adjustment of the particle diameter and the pore diameter of the spherical porous titanium oxide nanoparticles in accordance with the application thereof has not been easy.

THE PRIOR ART DOCUMENT

Non Patent Document

Non-Patent Document 1: Z. Liu et al. Chem. Eur. J. 2007, 13, 1851
Non-Patent Document 2: W.-G. Yang et al. J. Mater. Chem. 2010, 20, 2870
Non-Patent Document 3: Y. Yin et al. Anal. Chem. 2010, 82, 7249; Angew. Chem. Int. Ed. 2010, 49, 1862
Non-Patent Document 4: T. Adachiri et al. J. Am. Chem. Soc. 2007, 129, 11061. Dalton Trans., 2011, 40, 1073.
Non-Patent Document 5: T. Adschiri et al. J. Nanoparticle Res. 2007, 9, 1067; Chem Lett. 2010, 39, 981.

SUMMARY OF THE INVENTION

Problem(s) to be Solved by the Invention

The present invention is made to solve the problems described above, and it provides a method for synthesizing spherical porous titanium oxide nanoparticles, which is easy to operate, does not take a long time for synthesis, and can easily adjust the particle diameter and the pore diameter of the spherical porous titanium oxide nanoparticles in accordance with the application thereof; spherical porous titanium oxide nanoparticles produced by the synthesizing method; and a gene gun carrier consisting of the spherical porous titanium oxide nanoparticles.

Means for Solving the Problem(s)

A method for synthesizing spherical porous titanium oxide nanoparticles according to the present invention includes: a step of reacting titanium isopropoxide and carboxylic acid in supercritical fluid, wherein the supercritical fluid is supercritical methanol, and the carboxylic acid is formic acid, acetic acid, benzoic acid, o-phthalic acid, fumaric acid, or maleic acid.

In the method for synthesizing spherical porous titanium oxide nanoparticles according to one aspect of the present invention, benzamide is further added in the supercritical fluid in the step of reacting titanium isopropoxide and carboxylic acid in supercritical fluid.

In the method for synthesizing spherical porous titanium oxide nanoparticles according to one aspect of the present invention, erbium acetate tetrahydrate is further added in the supercritical fluid in the step of reacting titanium isopropoxide and carboxylic acid in supercritical fluid.

The spherical porous titanium oxide nanoparticles according to the present invention are produced by the method for synthesizing spherical porous titanium oxide nanoparticles according to the present invention.

The spherical porous titanium oxide nanoparticles according to one aspect of the present invention are produced by the method for synthesizing spherical porous titanium oxide nanoparticles according to one aspect of the present invention, and nitrogen is doped in the spherical porous titanium oxide nanoparticles.

The spherical porous titanium oxide nanoparticles according to one aspect of the present invention are produced by the method for synthesizing spherical porous titanium oxide nanoparticles according to one aspect of the present invention, and erbium is doped in the spherical porous titanium oxide nanoparticles.

A gene gun carrier according to the present invention consists of the spherical porous titanium oxide nanoparticles according to the present invention and the spherical porous titanium oxide nanoparticles according to one aspect of the present invention.

Effect of the Invention

Since the method for synthesizing spherical porous titanium oxide nanoparticles according to the present invention includes a step of reacting titanium isopropoxide and carboxylic acid in supercritical fluid, it can use one-pot synthesis, thus allowing the reaction time thereof to be shorter and the operation thereof to be easier. The use of supercritical methanol as supercritical fluid allows the synthesis of spherical porous titanium oxide nanoparticles without separating primary particles. The use of formic acid, acetic acid, benzoic acid, o-phthalic acid, fumaric acid, or maleic add as carboxylic acid allows the synthesis of spherical porous titanium oxide nanoparticles without separating primary particles. The use of supercritical methanol as supercritical fluid and the use of formic acid, acetic add, benzoic acid, o-phthalic acid, fumaric acid, or maleic acid as carboxylic add allow easy adjustment of the particle diameter and the pore diameter of the spherical porous titanium oxide nanoparticles for synthesis by adjusting the reaction temperature and the reaction time, so that the spherical porous titanium oxide nanoparticles having various properties can be synthesized in accordance with the application thereof.

According to one aspect of the method for synthesizing spherical porous titanium oxide nanoparticles of the present invention, spherical porous titanium oxide nanoparticles with nitrogen doped therein can be produced. Since these nitrogen-doped spherical porous titanium oxide nanoparticles absorb visible light (wavelength up to 500 nm), they can make a high efficient semiconductor.

According to one aspect of the method for synthesizing spherical porous titanium oxide nanoparticles of the present invention, spherical porous titanium oxide nanoparticles with erbium doped therein can be produced. These erbium-doped spherical porous titanium oxide nanoparticles emit green light when they are irradiated by light. Thus, they are expected to be used as cell marker for inorganic substance.

The gene gun carrier according to the present invention used for gene delivery can safely transfer genes into cells without affecting a living body. In addition, the gene gun carrier according to the present invention can be obtained at a cost lower than metallic particles such as gold and tungsten which are conventionally used as a gene gun carrier.

DETAILED DESCRIPTION OF THE INVENTION

Figure 1:
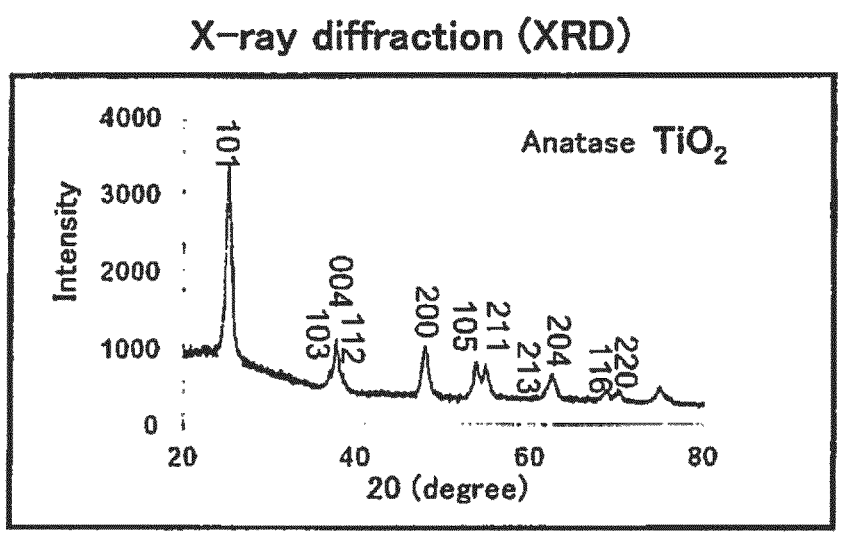
FIG. 1 is a result of X-ray diffraction of the spherical porous titanium oxide nanoparticles obtained in Example 1.

Hereinafter, a method for synthesizing spherical porous titanium oxide nanoparticles, spherical porous titanium oxide nanoparticles produced by the synthesizing method, and a W.G. Yang et al. *Contolling Synthesis of Well-Crystallized Mesoporous Microspheres Tio₂ Microspheres with Ultrahigh Surface Area for High-Performance Dye-Sensitized Solar Cells* J.Mater. Chem. 2010, 20, pp. 2870-2876.

T. Togashi et al. *Surfactant-Assisted One-Pot Synthesis of Superparamagnetic Magnetite Nanoparticle Cluster with Tunable Cluster Size and Magnetic Field Sensitivy* J. Am. Chem. Soc. 2007, 129, 11061, Dalton Trans., 2011, 40, pp. 1073-1078.

T. Arita et al. *Super Hydrothermal Synthesis of Carboxylic Acid—Surface-Functionalized TiO₂ Nanocrystals: pH Sensitive Dispersion and Hybridization with Organic Compounds* J. Nanoparticle Res 2007, 9, 1067; Chem Lett. 2010, 39, pp. 961-963. gene gun carrier consisting of the spherical porous titanium oxide nanoparticles according to the present invention will be described.

The method for synthesizing spherical porous titanium oxide nanoparticles according to the present invention is a method for synthesizing spherical porous titanium oxide nanoparticle including a step of reacting titanium isopropoxide and carboxylic acid in supercritical fluid. The supercritical fluid refers to a state in which a material is placed under the temperature and the pressure equal to or higher than the critical point, and is a state in which gas and liquid cannot be distinguished. Thus, it possesses diffusibility of gas and solubility of liquid. In the present invention, supercritical methanol is used as supercritical fluid. The use of the supercritical methanol allows the synthesis of spherical porous titanium oxide nanoparticles without separating primary particles.

Titanium isopropoxide is a kind of titanium alkoxide with CAS. No. 546-66-9. It is represented by the chemical formula Ti(O$^i$Pr)₄ ($^i$Pr is isopropyl group: —CH(CH₃)₂), and has a structure as shown in Formula 1 below.

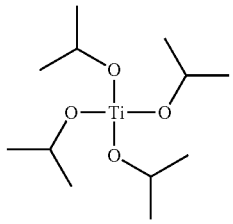

Formula 1

The concentration of titanium isopropoxide with respect to the methanol is preferably between 0.01 mol/L and 1.0 mol/L.

In the present invention, carboxylic acid which is reacted with titanium isopropoxide is formic add, acetic add, benzoic add, o-phthalic add, fumaric add, or maleic add.

Formic add is a kind of lower carboxylic add with CAS. No. 64-16-6. It is represented by the chemical formula HCOOH, and has a structure as shown in Formula 2 below.

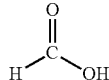

Formula 2

Acetic add is a kind of lower carboxylic add with CAS. No. 64-19-7. It is represented by the chemical formula CH₃COOH, and has a structure as shown in Formula 3 below.

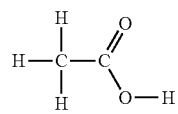

Formula 3

Benzoic add is a kind of aromatic carboxylic acid with CAS. No. 85-85-0. R is represented by the chemical formula C₈H₅COOH, and has a structure as shown in Formula 4

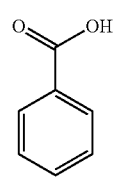

Formula 4

O-phthalic acid is a kind of aromatic carboxylic acid with CAS. No. 88-99-3. It is represented by the chemical formula C₆H₄(COOH)₂, and has a structure as shown in Formula 5 below.

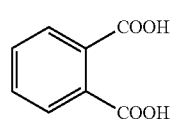

Formula 5

Fumaric acid is a kind of chain unsaturated carboxylic acid with CAS. No. 110-17-8. It shows trans-form of divalent carboxylic acid represented by the chemical formula C₂H₂(COOH)₂, and has a structure shown Formula 6 below.

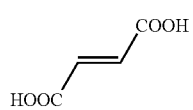

Formula 6

Maleic add is a kind of chain unsaturated carboxylic add with CAS. No. 110-16-7. It shows cis-form of divalent carboxylic add represented by the chemical formula C₂H₂(COOH)₂, and has a structure shown Formula 7 below.

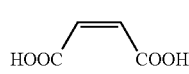

Formula 7

When the above-described carboxylic adds are reacted with titanium isopropoxide in supercritical methanol, spherical porous titanium oxide nanoparticles can be produced without separating primary particles. The concentration of the above-described carboxylic adds with respect to the methanol is preferably between 0.05 mol/L and 5.0 mol/L.

In the step of reacting titanium isopropoxide and carboxylic acid in supercritical fluid, benzamide can be added in supercritical methanol in addition to the above-described carboxylic acids. Thereby, spherical porous titanium oxide nanoparticles with nitrogen doped therein can be produced.

Benzamide is a compound with CAS. No. 55-21-0. It is represented by the chemical formula $C_6H_5CONH_2$, and has a structure shown in Formula 8 below.

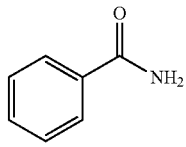

Formula 8

The concentration of benzamide with respect to the methanol is preferably between 1.0 molds and 3.0 mol/L. Since the nitrogen-doped spherical porous titanium oxide nanoparticles absorb visible light (wavelength up to 500 nm), they can make a high efficient semiconductor.

In the step of reacting titanium isopropoxide and carboxylic acid in supercritical fluid, erbium acetate tetrahydrate can be added in supercritical methanol in addition to the above-described carboxylic acids. Thereby, spherical porous titanium oxide nanoparticles with erbium doped therein can be produced.

Erbium acetate tetrahydrate is a compound with CAS. No. 15280-57-6. It is represented by the chemical formula $Er(CHCOO)_3 \cdot 4H_2O$, and has a structure shown in Formula 9 below.

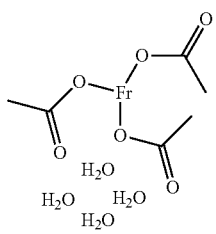

Formula 9

The concentration of erbium acetate tetrahydrate with respect to the methanol is preferably between 0.001 mol/L and 0.02 mol/L. The erbium doped spherical porous titanium oxide nanoparticles emit green light when they are irradiated by infrared-laser light. Thus, they are expected to be used as cell marker for inorganic substance.

In the present invention, the reaction temperature is preferably 200° C. and higher, and more preferably between 300° C. and 400° C. The reaction temperature lower than 200° C. is not preferable because the diameter of primary particles becomes small, and the pore diameter thereof becomes too small to form porous particles.

In the present invention, the reaction time is preferably at least one second, and more preferably between 1 minute and 10 minutes.

Spherical porous titanium oxide nanoparticles produced by the method for synthesizing spherical porous titanium oxide nanoparticles according to the present invention have an anatase-type crystalline structure.

Spherical porous titanium oxide nanoparticles according to the present invention can be used as a gene gun carrier. Since spherical porous titanium oxide nanoparticles according to the present invention do not affect a living body, they can be used as a carrier to safely transfer genes into cells. In addition, the gene gun carrier according to the present invention has an advantage that it can be obtained at a cost lower then metallic particles such as gold and tungsten which are conventionally used as a gene gun carrier. Targets into which genes are transferred include, but not limited to, unicellular algae such as *Chlamydomonas*.

EXAMPLES

The present invention will be described in more detail with reference to the following Examples. However, the method for synthesizing spherical porous titanium oxide nanoparticles, the spherical porous titanium oxide nanoparticles produced by the synthesizing method, and the gene gun carrier consisting of the spherical porous titanium oxide nanoparticles according to the present invention are not limited to the following Examples.

Example 1

Figure 2:
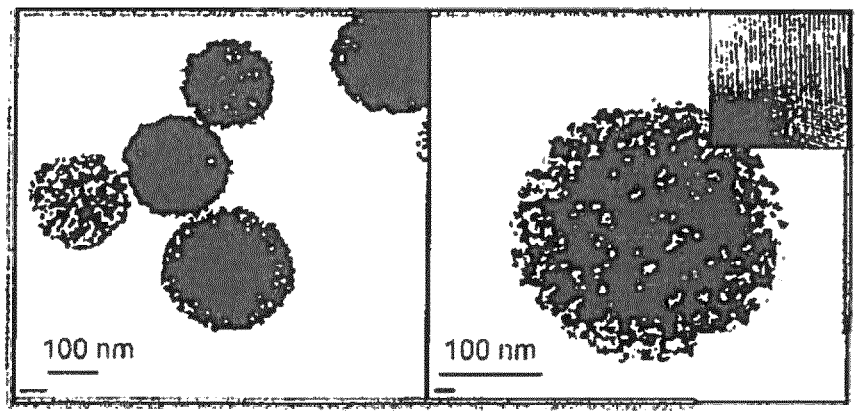
FIG. 2 is Transmission Electron Microscope (TEM) pictures of the spherical porous titanium oxide nanoparticles obtained in Example 1 dispersed in DMF.

Titanium isopropoxide 110 mg and methanol 3.5 mL were mixed, and orthophthalic acid 290 mg was added as an organic modifying agent so as to make a solution of 0.5 mol/L. This solution was heated up to 400° C. into supercritical methanol and reacted for 10 minutes. Thereafter, the solution was centrifuged, ultrasonic-washed using methanol, and then dried so as to obtain powder of spherical porous titanium oxide nanoparticles. A result of X-ray diffraction of the obtained spherical porous titanium oxide nanoparticles is shown in FIG. 1, and Transmission Electron Microscope (TEM) pictures of the spherical porous titanium oxide nanoparticles dispersed in DMF are shown in FIG. 2.

Example 2

Figure 3:
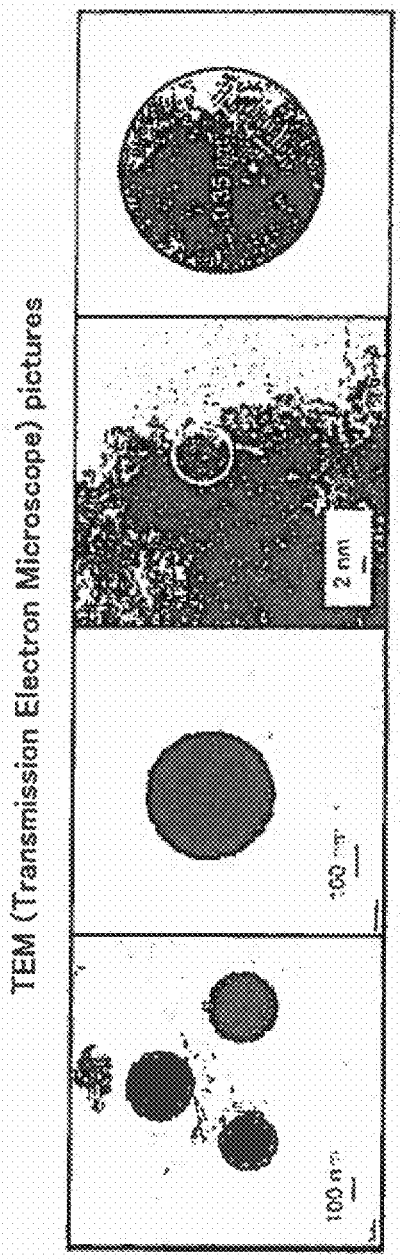
FIG. 3 is TEM pictures of the spherical porous titanium oxide nanoparticles obtained in Example 2 dispersed in DMF.

Powder of spherical porous titanium oxide nanoparticles was obtained under the same condition as Example 1 except that the reaction time was one minute in Example 2. TEM pictures of the spherical porous titanium oxide nanoparticles dispersed in DMF are shown in FIG. 3.

Example 3

Figure 4:
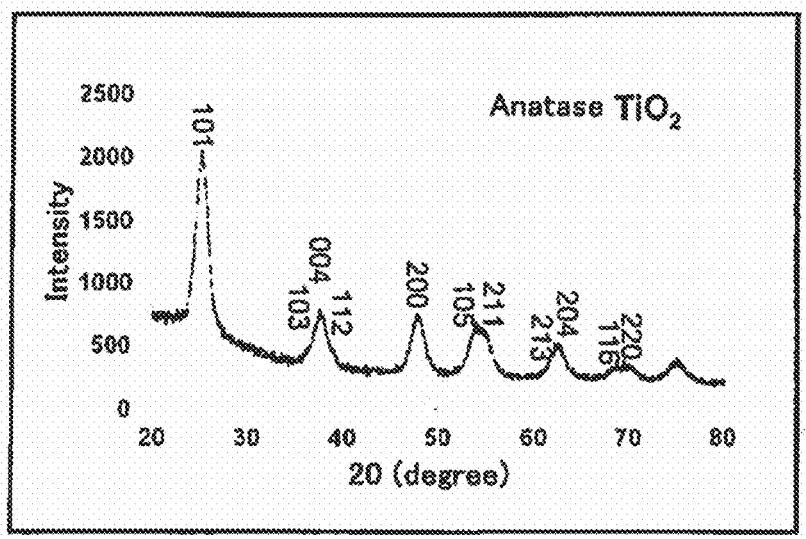
FIG. 4 is a result of X-ray diffraction of the spherical porous titanium oxide nanoparticles obtained in Example 3.
Figure 5:
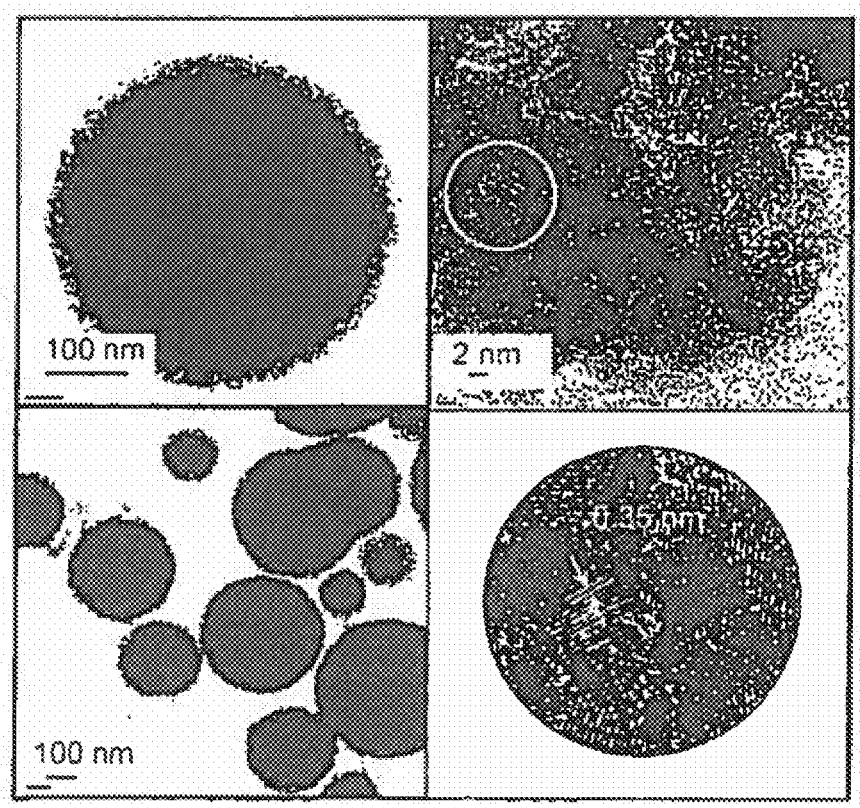
FIG. 5 is TEM pictures of the spherical porous titanium oxide nanoparticles obtained in Example 3 dispersed in DMF.

Powder of spherical porous titanium oxide nanoparticles was obtained under the same condition as Example 1 except that the reaction temperature was 300° C. in Example 3. A result of X-ray diffraction of the obtained spherical porous titanium oxide nanoparticles is shown in FIG. 4, and TEM pictures of the spherical porous titanium oxide nanoparticles dispersed in DMF are shown in FIG. 5.

Example 4

Figure 6:
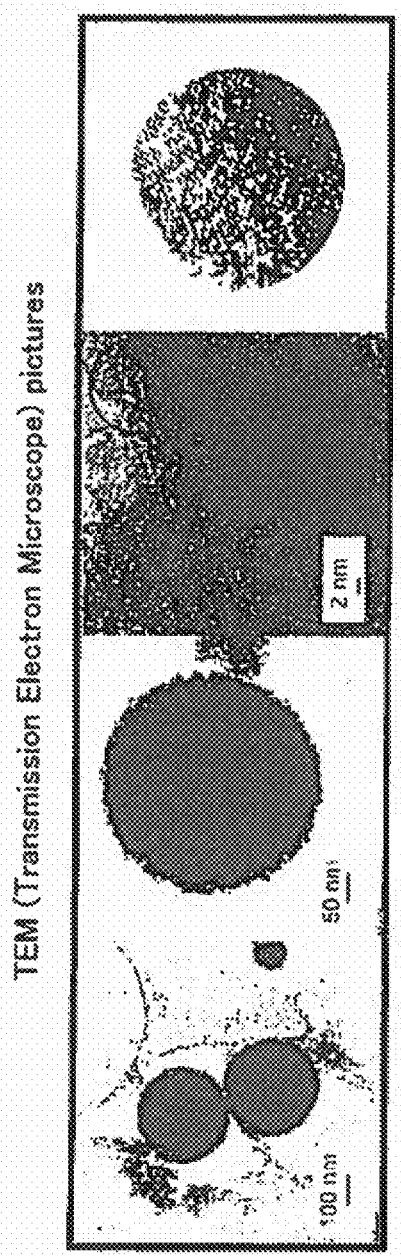
FIG. 6 is TEM pictures of the spherical porous titanium oxide nanoparticles obtained in Example 4 dispersed in DMF.

Powder of spherical porous titanium oxide nanoparticles was obtained under the same condition as Example 1 except that the reaction time was one minute and the reaction temperature was 300° C. in Example 4. TEM pictures of the spherical porous titanium oxide nanoparticles dispersed in DMF are shown in FIG. 6.

Example 5

Figure 7:
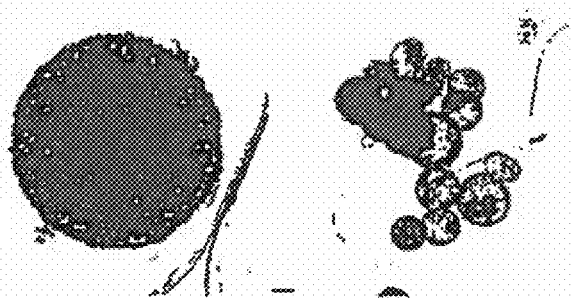
FIG. 7 is TEM pictures of the spherical porous titanium oxide nanoparticles obtained in Example 5 dispersed in DMF.

Powder of spherical porous titanium oxide nanoparticles was obtained under the same condition as Example 1 except that formic acid was used as the organic modifying agent in Example 5. TEM pictures of the spherical porous titanium oxide nanoparticles dispersed in DMF are shown in FIG. 7.

Example 6

Figure 8:
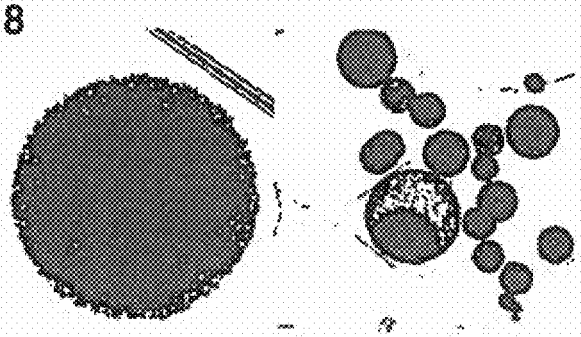
FIG. 8 is TEM pictures of the spherical porous titanium oxide nanoparticles obtained in Example 6 dispersed in DMF.

Powder of spherical porous titanium oxide nanoparticles was obtained under the same condition as Example 1 except that acetic acid was used as the organic modifying agent in Example 6. TEM pictures of the spherical porous titanium oxide nanoparticles dispersed in DMF are shown in FIG. 8.

Example 7

Figure 9:
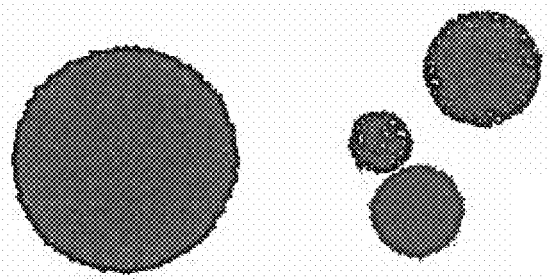
FIG. 9 is TEM pictures of the spherical porous titanium oxide nanoparticles obtained in Example 7 dispersed in DMF.

Powder of spherical porous titanium oxide nanoparticles was obtained under the same condition as Example 1 except that benzoic acid was used as the organic modifying agent in Example 7. TEM pictures of the spherical porous titanium oxide nanoparticles dispersed in DMF are shown in FIG. 9.

Example 8

Figure 10:
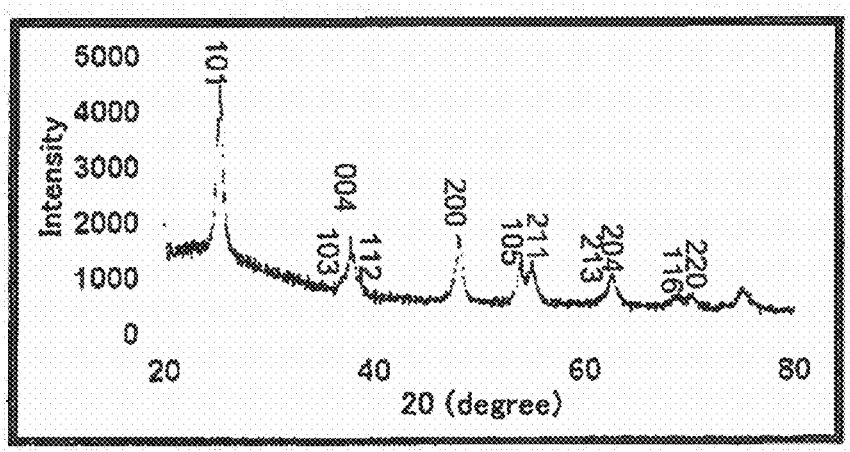
FIG. 10 is a result of X-ray diffraction of the spherical porous titanium oxide nanoparticles obtained in Example 8.
Figure 11:
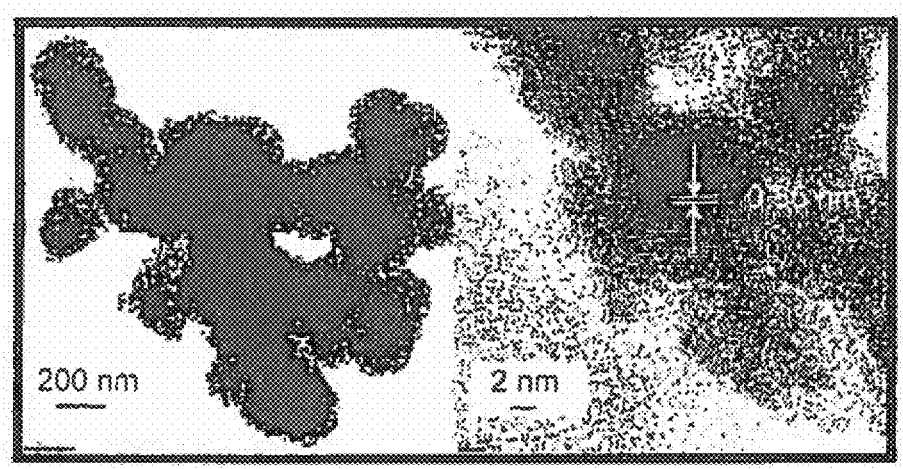
FIG. 11 is TEM pictures of the spherical porous titanium oxide nanoparticles obtained in Example 8 dispersed in DMF.

Powder of spherical porous titanium oxide nanoparticles was obtained under the same condition as Example 1 except that fumaric acid was used as the organic modifying agent in Example 8. A result of X-ray diffraction of the obtained spherical porous titanium oxide nanoparticles is shown in FIG. 10, and TEM pictures of the spherical porous titanium oxide nanoparticles dispersed in DMF are shown in FIG. 11.

Example 9

Figure 12:
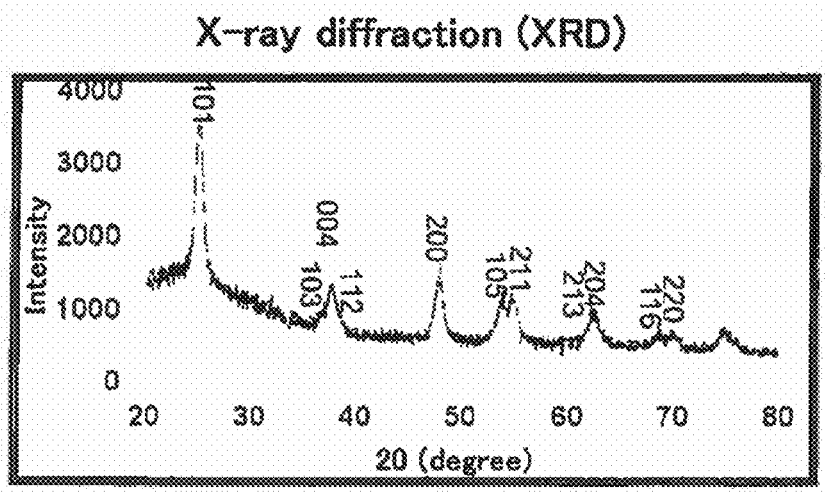
FIG. 12 is a result of X-ray diffraction of the spherical porous titanium oxide nanoparticles obtained in Example 9.
Figure 13:
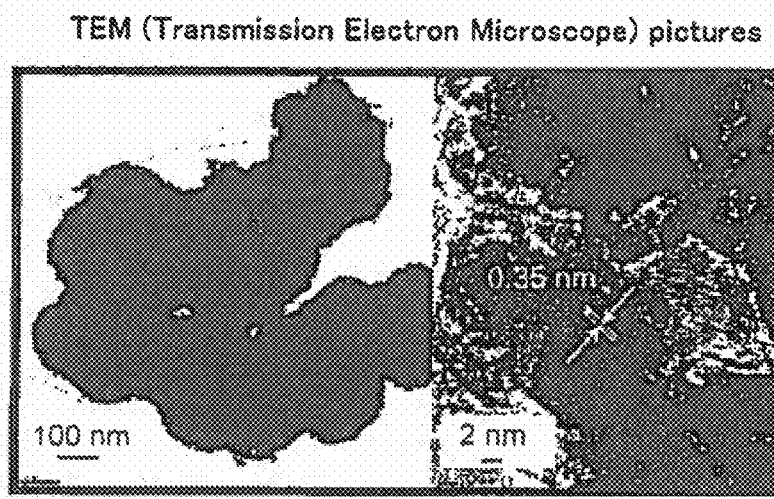
FIG. 13 is TEM pictures of the spherical porous titanium oxide nanoparticles obtained in Example 9 dispersed in DMF.

Powder of spherical porous titanium oxide nanoparticles was obtained under the some condition as Example 1 except that maleic acid was used as the organic modifying agent in Example 9. A result of X-ray diffraction of the obtained spherical porous titanium oxide nanoparticles is shown in FIG. 12, and TEM pictures of the spherical porous titanium oxide nanoparticles dispersed in DMF ere shown in FIG. 13.

Example 10

Figure 24:
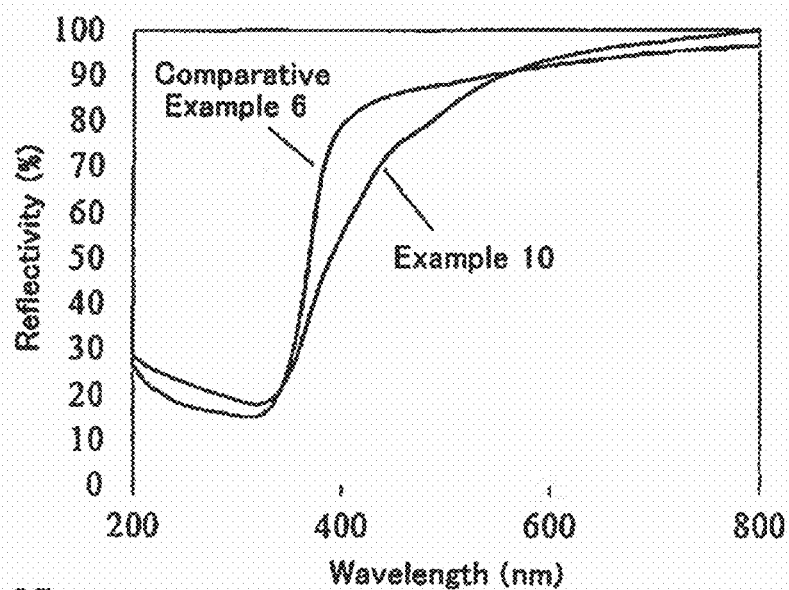
FIG. 24 is ultraviolet and visible reflection spectrums of the titanium oxide nanoparticles of Example 10 and Comparative Example 6.

0.33 mL (1 mmol) of titanium isopropoxide was added to 10 mL of methanol solution (0.5 mol/L) including 0.6230 g of benzoic acid while vigorously stirring titanium isopropoxide 0.33 mL (1 mmol). 2.5504 g (20 mmol) of benzamide was added to the solution and stirred overnight. 3.5 mL was measured off from the entire solution and transferred into the some SUS 316 reaction tube. Then, this solution was heated up to 400° C. into supercritical methanol and reacted for 60 minutes. Thereafter, the solution was centrifuged, ultrasonic-washed using methanol, and then dried so as to obtain powder of spherical porous titanium oxide nanoparticles. An ultraviolet and visible reflection spectrum of the spherical porous titanium oxide nanoparticles is shown in FIG. 24.

Example 11

Figure 25:
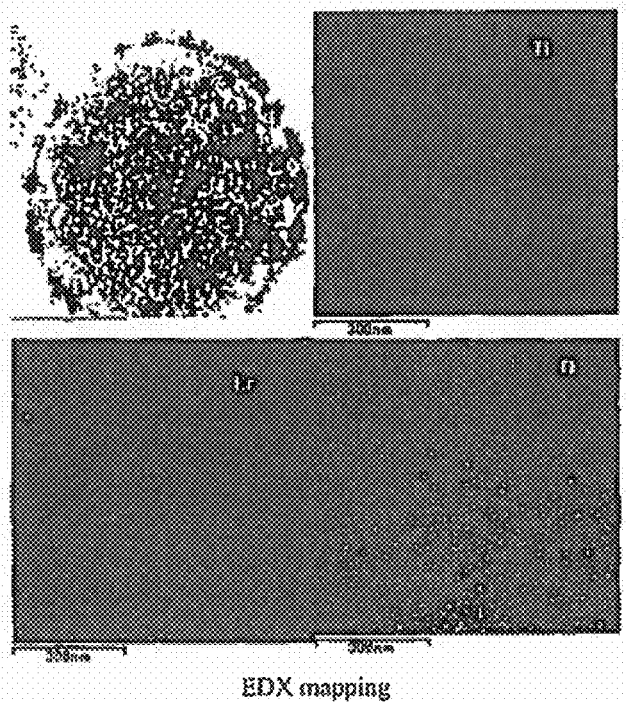
FIG. 25 is a TEM picture and EDX mapping of the titanium oxide nanoparticles obtained in Example 11 dispersed in DMF.

0.33 mL (1 mmol) of titanium isopropoxide was added to 10 mL of methanol solution (0.5 mol/L) including 300.3 mg of benzoic acid while vigorously stirring titanium isopropoxide 0.33 mL (1 mmol). 43.9 mg of erbium acetate tetrahydrate was added to the solution and stirred overnight. 3.5 mL was measured off from the entire solution and transferred into the same SUS 316 reaction tube. Then, this solution was heated up to 400° C. into supercritical methanol and reacted for 60 minutes. Thereafter, the solution was centrifuged, ultrasonic-washed using methanol, and then dried so as to obtain powder of spherical porous titanium oxide nanoparticles A. TEM picture and EDX mapping of the powder of the spherical porous titanium oxide nanoparticles are shown in FIG. 25.

Comparative Example 1

Figure 14:
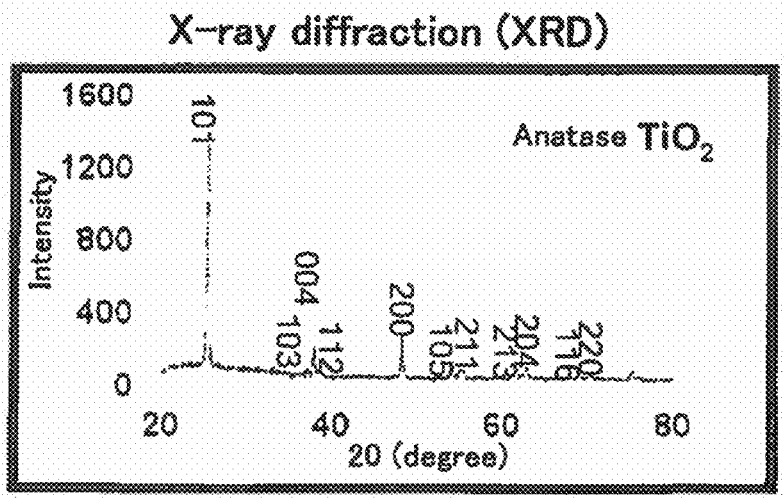
FIG. 14 is a result of X-ray diffraction of the titanium oxide nanoparticles obtained in Comparative Example 1.
Figure 15:
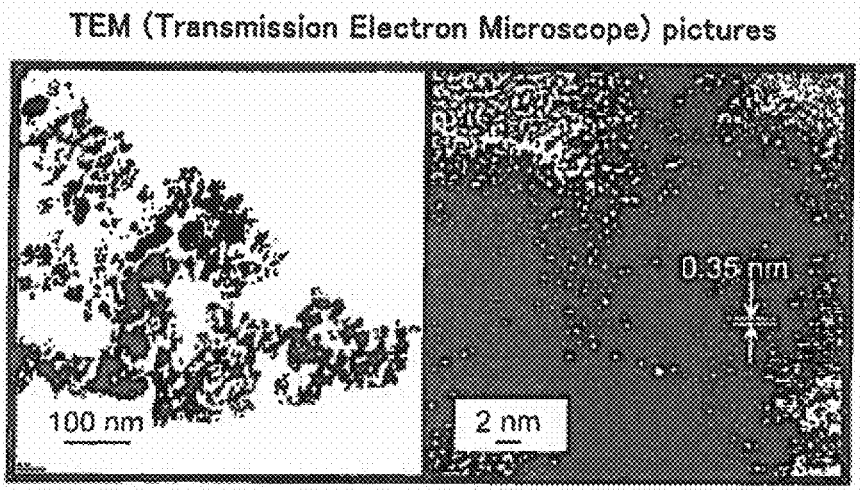
FIG. 15 is TEM pictures of the titanium oxide nanoparticles obtained in Comparative Example 1 dispersed in DMF.

Powder of titanium oxide nanoparticles was obtained under the same condition as Example 1 except that no organic modifying agent was added in Comparative Example 1. A result of X-ray diffraction of the obtained titanium oxide nanoparticles is shown in FIG. 14, and TEM pictures of the titanium oxide nanoparticles dispersed in DMF are shown in FIG. 15.

Comparative Example 2

Figure 16:
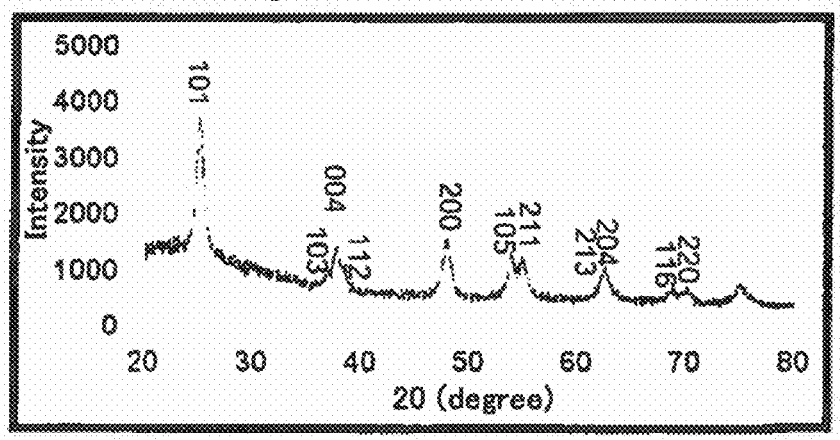
FIG. 16 is a result of X-ray diffraction of the titanium oxide nanoparticles obtained in Comparative Example 2.
Figure 17:
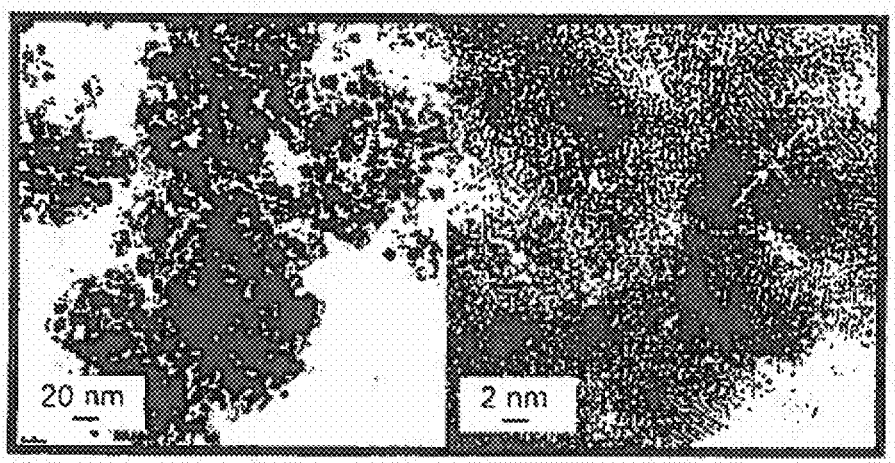
FIG. 17 is TEM pictures of the titanium oxide nanoparticles obtained in Comparative Example 2 dispersed in DMF.

Powder of titanium oxide nanoparticles was obtained under the same condition as Example 1 except that isoph-thalic acid (meta isomer of o-phthalic acid) was used as the organic modifying agent in Comparative Example 2. A result of X-ray diffraction of the obtained titanium oxide nanoparticles is shown in FIG. 16, and TEM pictures of the spherical porous titanium oxide nanoparticles dispersed in DMF are shown in FIG. 17.

Comparative Example 3

Figure 18:
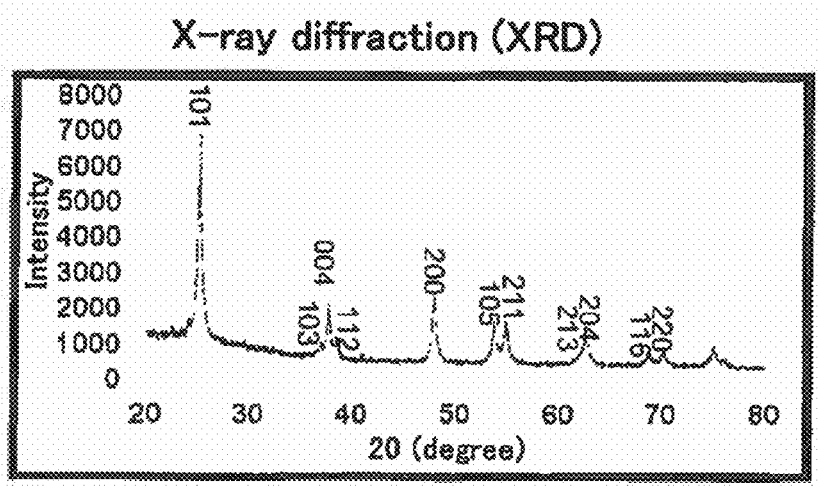
FIG. 18 is a result of X-ray diffraction of the titanium oxide nanoparticles obtained in Comparative Example 3.
Figure 19:
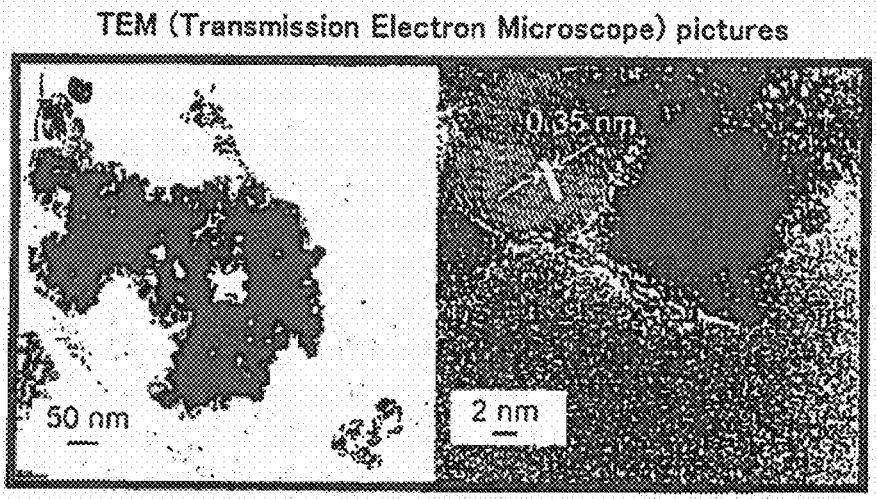
FIG. 19 is TEM pictures of the titanium oxide nanoparticles obtained in Comparative Example 3 dispersed in DMF.

Powder of titanium oxide nanoparticles was obtained under the same condition as Example 1 except that terephthalic acid (para isomer of o-phthalic acid) was used as the organic modifying agent in Comparative Example 3. A result of X-ray diffraction of the obtained titanium oxide nanoparticles is shown in FIG. 18, and TEM pictures of the spherical porous titanium oxide nanoparticles dispersed in DMF are shown in FIG. 19.

Comparative Example 4

Figure 20:
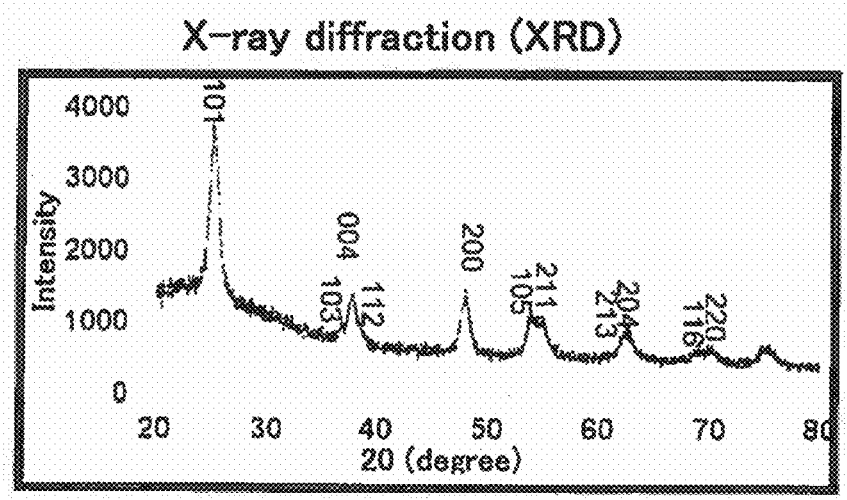
FIG. 20 is a result of X-ray diffraction of the titanium oxide nanoparticles obtained in Comparative Example 4.
Figure 21:
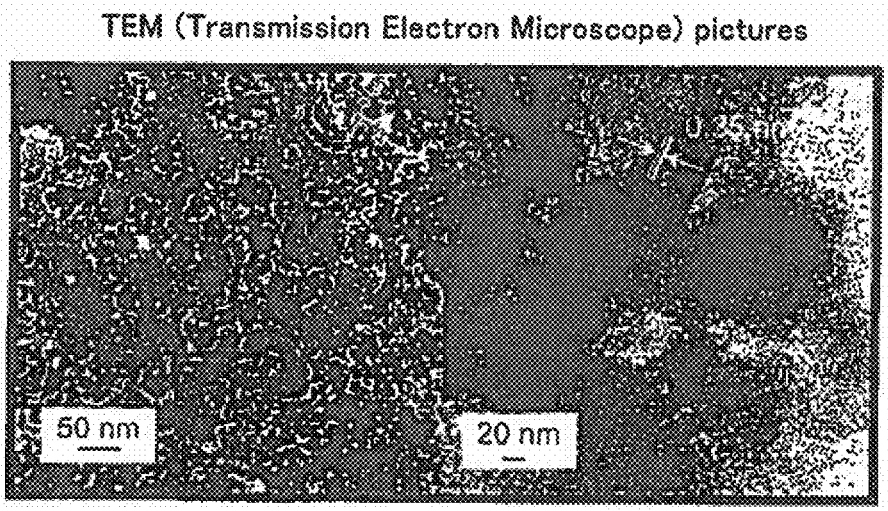
FIG. 21 is TEM pictures of the titanium oxide nanoparticles obtained in Comparative Example 4 dispersed in DMF.

Powder of titanium oxide nanoparticles was obtained under the same condition as Example 1 except that benzene-1,3,5-tricarboxylic acid was used as the organic modifying agent in Comparative Example 4. A result of X-ray diffraction of the obtained titanium oxide nanoparticles is shown in FIG. 20, and TEM pictures of the spherical porous titanium oxide nanoparticles dispersed in DMF are shown in FIG. 21.

Comparative Example 5

Figure 22:
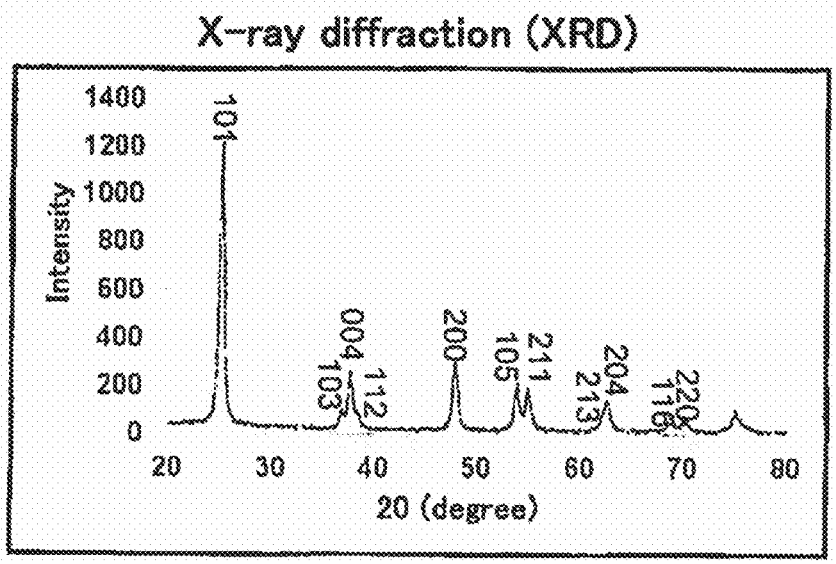
FIG. 22 is a result of X-ray diffraction of the titanium oxide nanoparticles obtained in Comparative Example 5.
Figure 23:
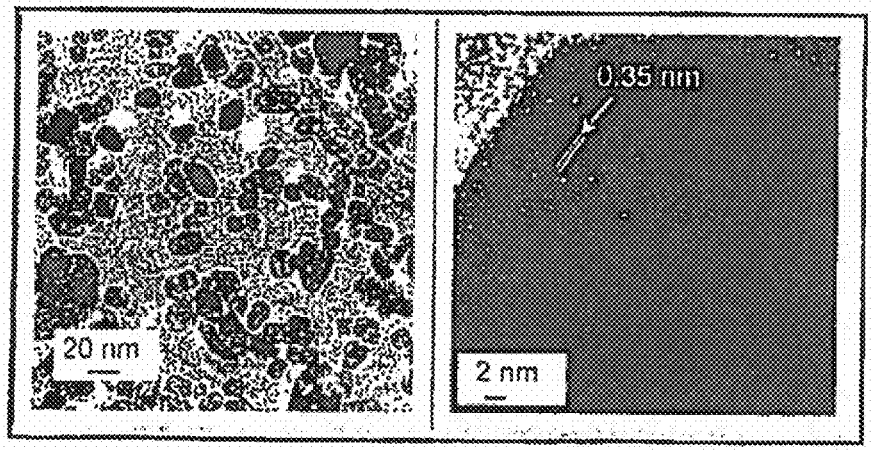
FIG. 23 is TEM pictures of the titanium oxide nanoparticles obtained in Comparative Example 5 dispersed in DMF.

Powder of titanium oxide nanoparticles was obtained under the same condition as Example 1 except that supercritical water was used in Comparative Example 5 instead of supercritical methanol. A result of X-ray diffraction of the obtained spherical porous titanium oxide nanoparticles is shown in FIG. 22, and TEM pictures of the titanium oxide nanoparticles dispersed in DMF are shown in FIG. 23.

Comparative Example 6

Powder of titanium oxide nanoparticles was obtained under the same condition as Example 10 except that benzamide was not added in Comparative Example 6. An ultraviolet and visible reflection spectrum of the spherical porous titanium oxide nanoparticles is shown in FIG. 24.

Results

As shown in the TEM pictures of FIGS. 2, 3, 5 to 9, 11, and 13, it is recognized that spherical porous titanium oxide nanoparticles are formed in Examples 1 to 9. On the other hand, as shown in the TEM pictures of FIGS. 15, 17, 19, 21, and 23, it is recognized that primary particles remain separate, and thus spherical porous titanium oxide nanoparticles are not formed in Comparative Examples 1 to 5. In addition, it is seen that some of the spherical porous titanium oxide nanoparticles of Example 5 (FIG. 7) and Example 6 (FIG. 8) using formic acid and acetic acid respectively as carboxylic acid are hollow, and in particular, it is recognized that most of the spherical porous titanium oxide nanoparticles of Example 5 (FIG. 7) using formic acid are hollow.

From this result, it is recognized that when methanol was used as supercritical fluid, and formic acid, acetic acid, benzoic acid, o-phthalic acid, fumaric acid, or maleic acid was used as carboxylic acid for en organic modifying agent, spherical porous titanium oxide nanoparticles can be formed.

When the TEM pictures (FIG. 2) of Example 1 (reaction temperature: 400° C.) and the TEM pictures (FIG. 5) of Example 3 (reaction temperature: 300° C.) are compared, it is recognized that the spherical porous titanium oxide nanoparticles formed in Example 1 has a larger diameter of the primary particle, has a larger pore diameter of the primary particle, and has coarser spherical porous titanium oxide nanoparticles than Example 3. On the other hand, it is recognized that the spherical porous titanium oxide nanoparticles formed in Example 3 has a smaller diameter of the primary particle, has a smaller pore diameter of the primary particle, and has finer spherical porous titanium oxide nanoparticles. Accordingly, it is recognized that as the reaction temperature becomes higher, spherical porous titanium oxide nanoparticles having a larger pore diameter can be formed. In addition, it is recognized that adjusting the reaction temperature allows for the adjustment of the pore diameter of spherical porous titanium oxide nanoparticles.

FIG. 24 shows ultraviolet and visible reflection spectrums of titanium oxide nanoparticles of Example 10 and Comparative Example 6, and FIG. 25 shows a TEM picture and EDX mapping of titanium oxide nanoparticles of Example 11. It is recognized from the ultraviolet and visible reflection spectrums of FIG. 24 that the titanium oxide nanoparticles of Example 10 and the titanium oxide nanoparticles of Comparative Example 6 show different ultraviolet and visible reflection spectrums. From this, it is recognized that nitrogen is doped in the titanium oxide nanoparticles of Example 10. It is difficult to tell since the pictures are not colored, but R is recognized from the EDX mapping of FIG. 25 that Ti, O, and Er are uniformly distributed across the spherical porous titanium oxide nanoparticles.

Transformation of unicellular green algae with $TiO_2$

The spherical porous titanium oxide nanoparticles obtained in Example 1 were used as a gene gun carrier to evaluate whether it is possible to transform the unicellular green algae as follows.

1 μg of annular pHyg3 plasmid (Berthold et al. 2002, Protist 153: 401-402) was transferred into cells (CC-124 strains), approximately $3 \times 10^7$, of *Chlamydomonas reinhardti* of logarithmic growth phase using a gene transfer apparatus of PDS-1000/He (Bio-Rad Laboratories, Inc.), and then the cells were sprayed on TAP agar medium containing 10 μg/mL of hygromycin B. The cells were cultured for 2 weeks at the temperature of 25° C. and at the illuminance of 1000 lux, and then the number of colonies on the agar was counted. As the carrier, the spherical porous titanium oxide nanoparticles having an average diameter of 0.3 μm obtained in Example 3 and the spherical porous titanium oxide nanoparticles having an average diameter of 0.26 μm obtained in Example 1 were used Table 1 shows a result of transformation using three kinds of gas pressures, and the number indicates the number of colonies on one plate. Six gene transfer operations were performed for each gas pressure. In addition, it was confirmed by amplification of DNA fragments using PCR method that the resulting colonies contained a portion of pHyg3 plasmid in their genome. Accordingly, in a wide range gas pressure, it was found that $TiO_2$ particles according to the present invention are suitable as a carrier of DNA.

TABLE 1

| Size of $TiO_2$ (average diameter) | He gas pressure (psi) | | |
| --- | --- | --- | --- |
| | 1100 | 1300 | 2000 |
| 0.3 μm (Example 3) | 12, 7, 7, 5, 5, 3 | 9, 5, 3, 2, 2, 2 | 12, 10, 5, 5, 5, 4 |
| 0.26 μm (Example 1) | 21, 14, 7, 5, 2, 2 | 10, 8, 8, 1, 1, 1 | 10, 9, 6, 6, 5, 5 |

Figure 26:
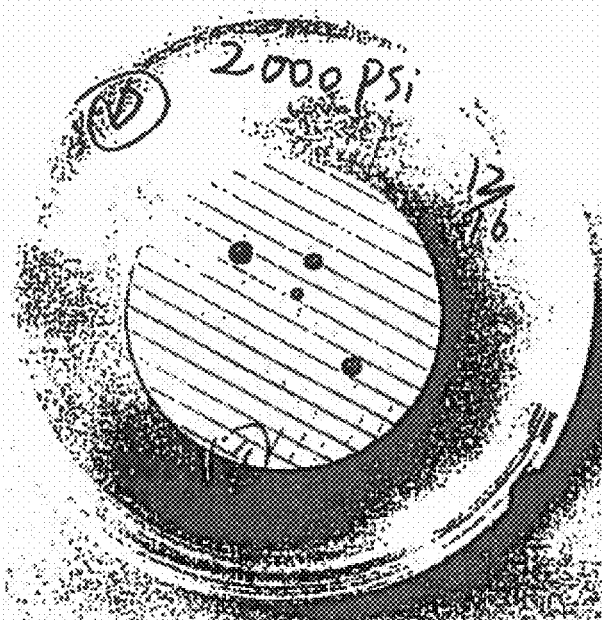
FIG. 26 is a picture showing a transformant obtained by using a gene gun having 0.3 μm of the titanium oxide particles as a carrier at the gas pressure of 2000 psi.

FIG. 26 is a picture showing a transformant obtained by using a gene gun having 0.3 μm of the titanium oxide particles as s carrier et the gas pressure of 2000 psi.

It is recognized that s portion of pHyg3 plasmid of all four transformants was amplified by PCR method.

INDUSTRIAL APPLICABILITY

The present invention is suitably used for white pigment, catalyst support, reaction catalyst, optical catalyst, solar battery, optical semiconductor, gene delivery reagent, cell marker, drug delivery agent, liquid crystal spacer, and the like.

The invention claimed is:

1. A method for synthesizing spherical porous titanium oxide nanoparticles, comprising:
   a step of reacting titanium isopropoxide and carboxylic acid in supercritical fluid, wherein
   the supercritical fluid is supercritical methanol, and
   the carboxylic acid is formic acid, acetic acid, benzoic acid, o-phthalic acid, fumaric acid, or maleic acid.

2. The method for synthesizing spherical porous titanium oxide nanoparticles according to claim 1, wherein
   in the reacting step, benzamide is further added in the supercritical fluid.

3. The method for synthesizing spherical porous titanium oxide nanoparticles according to claim 1, wherein
   in the reacting step, erbium acetate tetrahydrate is further added in the supercritical fluid.

4. The method of claim 1, wherein
   erbium is doped in the spherical porous titanium oxide nanoparticles.

5. The method of claim 4, wherein
   in the reacting step, erbium acetate tetrahydrate is further added in the supercritical fluid.

6. The method of claim 1, wherein
   nitrogen is doped in the spherical porous titanium oxide nanoparticles.

7. The method of claim 3, wherein
   nitrogen is doped in the spherical porous titanium oxide nanoparticles.

8. The method of claim 1, wherein a gene is added to the spherical porous titanium oxide nanoparticles.

9. The method of claim 8, wherein the method includes transporting the gene in the spherical porous titanium oxide nanoparticles.

10. The method of claim 1, wherein the carboxylic acid is formic acid.

11. The method of claim 1, wherein the carboxylic acid is acetic acid.

12. The method of claim 1, wherein the carboxylic acid is benzoic acid.

13. The method of claim 1, wherein the carboxylic acid is o-phthalic acid.

14. The method of claim 1, wherein the carboxylic acid is fumaric acid.

15. The method of claim 1, wherein the carboxylic acid is maleic acid.

* * * * *